US00PP22810P2

(12) United States Plant Patent
Egger

(10) Patent No.: US PP22,810 P2
(45) Date of Patent: Jun. 19, 2012

(54) ***SEDUM* PLANT NAMED 'BEACH PARTY'**

(50) Latin Name: ***Sedum* sp.**
Varietal Denomination: Beach Party

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/930,866

(22) Filed: Jan. 19, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Kent L Bell
(74) *Attorney, Agent, or Firm* — Jondle & Associates, P.C.

(57) ABSTRACT

A new and distinct hybrid of *Sedum* plant substantially as shown and described, with pink flowers in large inflorescences, cut and dark leaf margins, new leaves that are glossy, yellow green tinted red brown on the margins, strongly upright stems, and a low, clumping habit.

1 Drawing Sheet

Botanical denomination: *Sedum* sp.

Variety designation: 'Beach Party'.

Parentage: *Sedum telephium* dark leaf×*Sedum spectabile* 'Neon'.

Cross reference: *Sedum* 'Birthday Party' (U.S. Plant patent application Ser. No. 12/930,852).

The present invention relates to a new and distinct cultivar of *Sedum* and given the cultivar name of 'Beach Party'. *Sedum* is in the family Crassulaceae. *Sedum* 'Beach Party' originated from a cross between an unnamed, proprietary, and unpatented dark leaf *Sedum telephium* as the seed parent and *Sedum spectabile* 'Neon', unpatented, as the pollen parent.

Compared to the dark leaf *Sedum telephium* seed parent, 'Beach Party' has much greener foliage and much larger inflorescence.

Compared to the pollen parent, *Sedum spectabile* 'Neon', 'Beach Party' has leaves that are glossier and tinted red-brown on the margins, whereas 'Neon' has leaves that are glaucous and evenly yellow.

Compared to *Sedum* 'Mr. Goodbud' (U.S. Plant Pat. No. 17,671), the new variety is shorter with leaves that are darker and more cut on the margins. The flowers of the new variety are lighter.

Compared to *Sedum* 'Birthday Party' (U.S. Plant patent application Ser. No. 12/930,852) the new variety has lighter flower color, and a slightly larger habit.

This new and unique *Sedum* is distinguished by:

1. pink flowers in large inflorescences,
2. cut and dark leaf margins,
3. new leaves that are glossy, yellow green tinted red brown on the margins,
4. strongly upright stems, and
5. a low, clumping habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 2 year old *Sedum* 'Beach Party' growing in a 2 gallon container outside in May in Canby, Oreg.

FIG. 2 shows a land a half year old *Sedum* 'Beach Party' growing in the garden in September in Canby, Oreg.

DETAILED PLANT DESCRIPTION

The following is a detailed description of the new *Sedum* hybrid based on observations of two year old specimens grown in a the garden in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:

*Type*.—Herbaceous perennial.
*Hardiness*.—USDA Zone 4 to 9.
*Size*.—17 to 28 cm tall from the ground to the base of the inflorescence and 43 cm wide.
*Habit*.—Erect, clumping.
*Vigor*.—Excellent.

Stem:

*Number*.—About 18.
*Size*.—30 cm long and 10 mm wide.
*Internode length*.—1 cm to 3 cm long.
*Color*.—Greyed Yellow 160C heavy tinted Greyed Orange 176A.
*Texture*.—Succulent.
*Surface* (*both upper and lower surfaces*).—Glabrous and glossy.

Leaf:

*Type*.—Simple.
*Arrangement*.—Variable.
*Shape*.—Elliptic to slightly obovate.

*Apex*.—Acute to obtuse.
*Base*.—Cuneate.
*Venation*.—Pinnate.
*Venation color* (*both upper and lower surfaces*).—Yellow Green 147C.
*Margins*.—Irregularly serrate.
*Blade size*.—Grows to 9 cm long and 4.7 cm wide.
*Surface*.—Glabrous, glossy when young.
*Texture*.—Thick, spongy, succulent.
*Petiole*.—Leaves sessile.
*Leaf color*.—Topside between Green N137A and 139A; bottom side closest to N138B.

Inflorescence:
*Type*.—Terminal, corymbose, umbel-like.
*Number of flowers*.—Over a 1000 per stem (increases with age).
*Pedicels*.—1 mm to 3 mm long, 1 mm wide, glaucous, Greyed Red 182B.
*Peduncle*.—8 to 10 cm tall and grows to 9 mm wide, Greyed Purple 183D, succulent, glabrous.
*Size*.—Grows to 19 cm deep and 15 cm wide.
*Bloom period*.—August through September in Canby, Oreg.

Flower bud:
*Size*.—2.5 mm wide, 6 mm deep.
*Description*.—Ovoid.
*Color*.—White N155B.

Flower:
*Type*.—Complete, actinomorphic.
*Shape*.—Stellate.
*Size*.—6 mm deep and 11 mm wide.
*Color*.—Purple 76D.
*Corolla description*.—6 mm deep and 11 mm wide, 5 petals, each lanceolate, 6 mm long and 1.5 mm wide, margins entire, tip acuminate, glabrous on both sides, topside Purple 76D, bottom side Purple 76B.
*Calyx description*.—2.5 mm deep and 2.5 mm wide, campanulate, 5 lobes, divided to the base, margins entire, tip acute, glabrous, Greyed Green 194A on both sides.
*Stamen description*.—10 in number, 7 mm long, filaments 7 mm long, Purple 77B, anthers Purple N77A, no pollen, male sterile.
*Pistil description*.—5 separate prominent carpels, each 6 mm deep and 1.5 mm wide, Purple 77B on top half to White NN155B on bottom half; style 2 mm long and Purple 77B, stigma rounded and Greyed Purple 187A.
*Fragrance*.—None.
*Lastingness*.—Each stem lasts up to a month.

Fruit:
*Type*.—Ventrally dehiscent follicle, erect, attenuate.
*Fertility*.—None.
*Color*.—Greyed Purple 187A at top and gray tan at bottom, Grey 200B.

Seed: No seed produced.

Disease and pest resistance or tolerance: Pest and disease resistance are typical for this type of *Sedum*.

I claim:

1. A new and distinct hybrid of *Sedum* plant as herein illustrated and described.

* * * * *

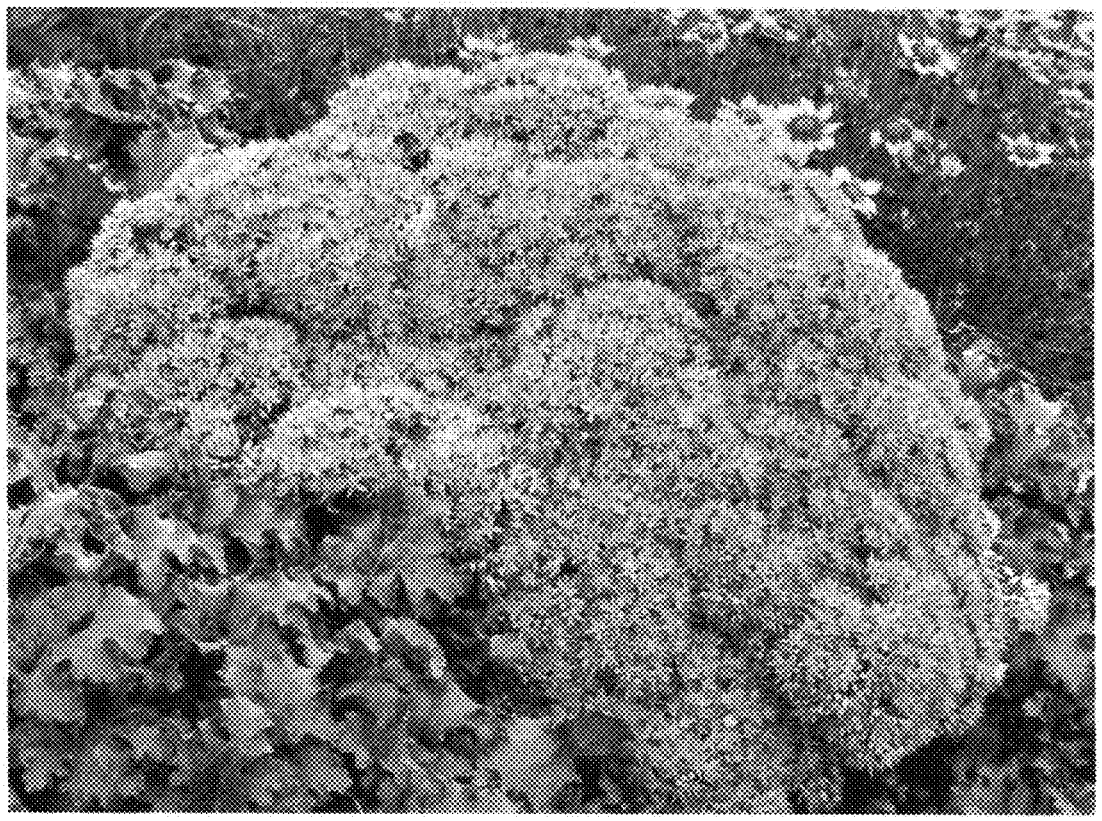

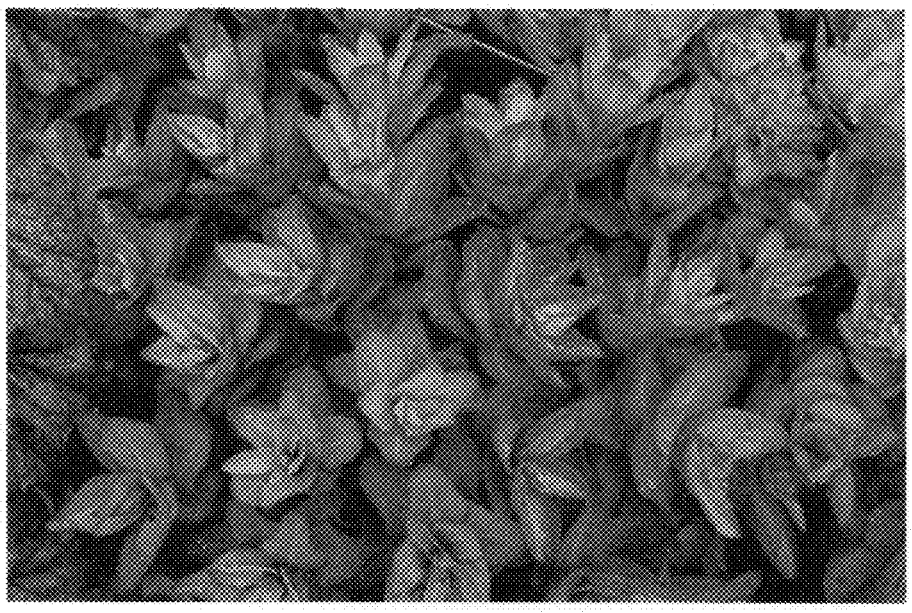
Figure 1 above, Figrure 2 below.